United States Patent [19]

Rae et al.

[11] Patent Number: 4,904,676
[45] Date of Patent: Feb. 27, 1990

[54] AMINO-OXAZOLE COMPOUNDS HAVING DOPAMINERGIC ACTIVITY

[75] Inventors: Duncan R. Rae, Lanark; Samuel G. Gibson, Motherwell, both of Scotland

[73] Assignee: Akzo N.V., Arnhem, Netherlands

[21] Appl. No.: 228,856

[22] Filed: Aug. 3, 1988

Related U.S. Application Data

[63] Continuation of Ser. No. 40,458, Apr. 20, 1987, abandoned.

[30] Foreign Application Priority Data

Apr. 29, 1986 [GB] United Kingdom ............... 8610432

[51] Int. Cl.⁴ .............................................. A61K 31/42
[52] U.S. Cl. ..................................... 514/340; 546/275
[58] Field of Search ............... 546/275, 280; 514/340, 514/342

[56] References Cited

U.S. PATENT DOCUMENTS 3,933,840  1/1976  Dahm et al. ..................... 546/198
4,413,001  11/1983 Bourgery et al. ................. 546/275
4,650,805  3/1987  Jaen et al. ....................... 514/342

*Primary Examiner*—Mary C. Lee
*Assistant Examiner*—Zinna Northington Davis
*Attorney, Agent, or Firm*—William M. Blackstone

[57] ABSTRACT

The present invention relates to new amino-thiazole and amino-oxazole derivatives of the general formula:

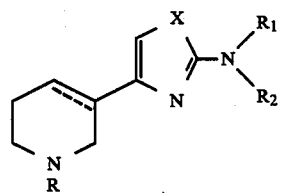

wherein:

R represents hydrogen, a lower alkyl group with 1 to 4 carbon atoms, a lower alkenyl group, a phenyl-alkyl (1–4 C), furanyl-alkyl (1–4 C) or thienyl-alkyl (1–4 C) group;
X represents sulphur or oxygen;
$R_1$ and $R_2$ represent hydrogen or alkyl (1–4 C), and the dotted line represents an optional extra bond, as well as pharmaceutically acceptable acid addition salts thereof, having potent dopamine-agonist activity.

4 Claims, No Drawings

AMINO-OXAZOLE COMPOUNDS HAVING DOPAMINERGIC ACTIVITY

This is a continuation of application Ser. No. 07,040,458 filed Apr. 20, 1987, now abandoned.

The present invention relates to new amino-thiazole and amino-oxazole derivatives. More particularly the invention refers to amino-thiazole and amino-oxazole derivatives of the general formula:

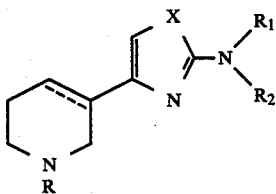

wherein:
R represents hydrogen, a lower alkyl group with 1 to 4 carbon atoms, a lower alkenyl group, a phenyl alkyl (1–4 C), furanyl alkyl (1–4 C) or thienyl alkyl (1–4 C) group;
X represents sulphur or oxygen;
$R_1$ and $R_2$ represent hydrogen or alkyl (1–4 C), and the dotted line represents an optional extra bond, as well as pharmaceutically acceptable acid addition salts thereof.

The invention also refers to methods for the preparation of the above new compounds and to pharmaceutical preparations containing same.

The compounds of formula I have very potent dopamine-agonist activity; they are therefore useful, for example, in the treatment of CNS disorders such as Schizophrenia, Parkinson disease or depression, in the treatment of cardiovascular diseases, such as hypertension and in the treatment of hyperprolactinemia.

The compounds of formula I can be prepared most conveniently by a partial or complete hydrogenation of a compound of the formula:

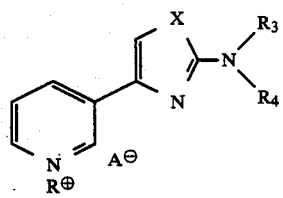

wherein
X and R, have the afore said meanings,
$A^-$ is any suitable anion, such as a halogen or hydroxy anion, and
$R_3$ and $R_4$ have the same meaning as $R_1$ and $R_2$ but may in addition represent an amino-protecting group or an aliphatic acyl group with 1–4 carbon atoms.

This partial or complete hydrogenation is carried out in the usual manner for example with the aid of complex metal hydrides such as sodiumborohydride or lithiumaluminiumhydride, by means of catalytic hydrogenation using a suitable catalyst or by other well known hydrogenation means such as sodiumdithionite.

If one or both substituents ($R_3$, $R_4$) at the nitrogen stand(s) for a N-protecting group, this protecting group may additionally be removed by well known methods for the removal of N-protecting groups such as hydrolysis or reduction.

Where $R_3$ or $R_4$ is an aliphatic acyl group with 1–4 carbon atoms, this group may be reduced to convert the said acyl group into an alkyl group (1–4 C).

The starting compounds of formula II can be obtained by quaternising in the usual manner a compound of the formula III

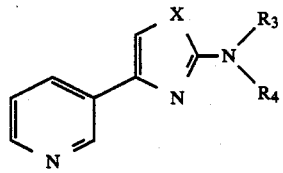

with the compound RA, in which X, R, $R_3$, $R_4$ and A have the afore said meanings. The compound of formula III has been described already in the literature.

The primary amino compounds of formula I ($R_1$ and/or $R_2$=hydrogen) may subsequently be alkylated in the usual manner, for example by reacting the compound with alkyl halide or by acylation followed by reduction of the carbonyl moiety to introduce the substituents $R_1$ and/or $R_2$.

For the introduction of a methyl group (at the nitrogen atom) the method of Eschweiler-Clarke or the reaction with formaldehyde or haloformic esters, followed by reduction is to be preferred.

Where the dotted line does not represent an extra bond, such compounds of formula I contain an asymetric centre. As a result thereof a racemic mixture, as well as separate optical isomers of formula I are possible. Both the racemic mixture as well as the separate optical isomers are numbered among the compounds of the invention.

The resolution of the racemic mixture of formula I is to be carried out in the usual manner e.g. with the aid of an optically active acid such as (+) or (−) tartaric acid.

The novel compounds of formula I may be isolated from the reaction mixture in the form of a pharmaceutically acceptable salt, dependent on the conditions in which the reaction is carried out. The pharmaceutically acceptable salts may also be obtained by treating the free base I with an organic or inorganic acid such as HCl, HBr, HI, $H_2SO_4$, $H_3PO_4$, acetic acid, propionic acid, glycolic acid, maleic acid, malonic acid, succinic acid, tartaric acid, citric acid, benzoic acid, ascorbic acid etc.

The term "alkyl" used in the definition of $R_1$ and $R_2$ means a saturated branched or unbranched hydrocarbon radical with 1–4 carbon atoms, such as methyl, ethyl, n.propyl, isopropyl, and n-butyl.

The term "alkyl" in the definition of R has a similar meaning as described for $R_1$ and $R_2$ but in addition includes a cyclopropylmethyl moiety.

The term "alkenyl" used in the definition of R means an unsaturated branched or unbranched hydrocarbon radical with 2 to 4 carbon atoms such as vinyl, 1-propenyl or allyl.

The compounds of the invention may be administered enterally or parenterally, preferably in a daily dosage of from 0.01–50 mg per kg bodyweight.

Mixed with suitable auxiliaries the compounds I may be compressed into solid dosage units, such as pills, tablets and coated tablets or be processed into capsules.

By means of suitable liquids the compounds I can also be applied as an injection preparation in the form of solutions, suspensions or emulsions or in the form of a spray, e.g. a nasal spray.

Preferred compounds according to the invention have the general formula I in which whether or not in combination:
(1) the dotted line does represent an extra bond;
(2) the meaning of X is sulphur;
(3) both $R_1$ and $R_2$ represent hydrogen, and
(4) R represents methyl, ethyl, n.propyl, allyl or cyclopropylmethyl.

If at least one of the symbols $R_1$ or $R_2$ represents hydrogen, the compounds of formula I exist in two tautomeric forms represented by the following equilibrium:

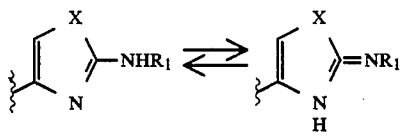

Both tautomers are numbered among the compounds of the invention.

EXAMPLES

Example 1

A. 1-Methyl-3-(2-amino-thiazol-4-yl)pyridinium bromide

A suspension of 3-(2-amino-thiazol-4-yl)pyridine (12.84 g) in acetonitrile (450 ml) containing bromomethane (6.84 g) was heated in stirring autoclave at 90° C. for 20 h.

The mixture was allowed to cool and the supernatant acetonitrile solution was decanted off and evaporated to dryness. The crystalline material remaining in the autoclave was dissolved in methanol and the solution evaporated to dryness. The total crude material recovered from the reaction was combined, and the product (17.05 g) crystallised from methanol and dried in vacuo at 70° C.

B. 4-(1-Methyl-1,2,5,6-tetrahydropyrid-3-yl)-thiazole-2-amine (Z)-2-butenedioate (1:1 salt)

Sodium borohydride (24.88 g) was added carefully to a solution of 1-methyl-3-(2-amino-thiazol-4-yl)pyridinium bromide (18.68 g) in methanol (540 ml), maintained at 10°-20° C. by cooling with an ice-bath. The reaction was then stirred at room temperature for 3.5 h.

The solution was neutralised by careful addition of glacial acetic acid. The methanol was removed by distillation under reduced pressure and the residue then diluted with water (650 ml), basified with 7% aqueous ammonia solution and the product precipitated by saturating the solution with sodium chloride.

The material was extracted with ethyl acetate (2×350 ml), dried ($Na_2SO_4$) and the solvent evaporated off to give an off-white crystalline solid (10–12 g), which was crystallised from methanol. M.p. 115°-116° C.

This material was dissolved in methanol and added to a solution of (Z)-2-butenedioic acid (6.02 g) in methanol. The resulting solution was decolourised by stirring with Norit charcoal (1.6 g) at room temperature and the charcoal removed by filtration through dicalite. The filtrate was evaporated to dryness under reduced pressure and the product (8.92 g, m.p. 173°-174° C.) crystallised from methanol, and dried in vacuo at 70° C.

Example 2

1-Propyl-3-(2-amino-thiazol-4-yl)piperidine (E)-2-butenedioate (2:1 salt)

A solution of 1-propyl-3-(2-amino-thiazol-4-yl)pyridinium bromide (12.42 g) in methanol (442 ml), water (884 ml) containing sodium dithionite (50.85 g) and sodium carbonate (46.8 g) was refluxed under nitrogen for 2.5 h. The methanol was distilled off under reduced pressure and the aqueous solution was acidified with 5N hydrochloric acid. The solution was then basified with 7% aq. ammonia and saturated with sodium chloride to precipitate the product. The material was extracted twice with ethyl acetate (2×35 ml), dried ($Na_2SO_4$) and the solvent was evaporated off under reduced pressure to give the product (6.15 g).

The material was chromatographed on a silica column (180 g), eluting with chloroform:ether:methanol:33% ammonia in the proportions 7:1.5:0.8:0.1. The fractions containing the major product, free from back-running impurity were combined and evaporated to dryness under reduced pressure. Weight=4.85 g.

This material was dissolved in methanol and added to a solution of (E)-2-butenedioic acid (2.52 g) in methanol. The resulting solution was decolourised stirring with Norit charcoal (730 mg) at room temperature and the charcoal was removed by filtration through dicalite. The filtrate was evaporated to dryness under reduced pressure and the product (3.4 g, m.p. 233° C. decomp.) was obtained after two recrystallisations from methanol.

Example 3

In an analogous manner as described in Example 1 were prepared:
1. 4-(1-Propyl-1,2,5,6-tetrahydropyrid-3-yl)-thiazole-2-amine (E)-2-butenedioate (2:1 salt), m.p. 248° C. (decomp.). (Free base m.p. 130°-131° C., the (Z)-2-butenedioate salt m.p. 188° C.);
2. 4-(1-butyl-1,2,5,6-tetrahydropyrid-3-yl)-thiazol-2-amine (Z)-2-butenedioate (2:3);
3. 4-(1-propyl-1,2,5,6-tetrahydropyrid-3-yl)-oxazol-2-amine (E)-2-butenedioate, m.p. 227°-231° C. (dec.);
4. 4-(1-methyl-1,2,5,6-tetrahydropyrid-3-yl)-oxazol-2-amine (Z)-2-butenedioate;
5. 4-[1-(propen-2-yl)-1,2,5,6-tetrahydropyrid-3-yl]-thiazole-2-amine (E)-2-butenedioate, m.p. 244°-246° C.;
6. 4-(1-ethyl-1,2,5,6-tetrahydropyrid-3-yl)-thiazole-2-amine (Z)-2-butenedioate (1:1) salt, m.p. 150°-152° C.;
7. N-methyl-4-(1-propyl-1,2,5,6-tetrahydropyrid-3-yl)-thiazole-2-amine (E)-2-butenedioate (1:1), m.p. 74°-78° C.;
8. 4-(1-cyclopropylmethyl-1,2,5,6-tetrahydropyrid-3-yl)-thiazole-2-amine (Z)-2-butenedioate (1:1), m.p. 199° C.
9. 4-[1-(2-phenylethyl)-1,2,5,6-tetrahydropyrid-3-yl]-thiazole-2-amine (E)-2-butenedioate (2:1), m.p. 185°-186° C.

We claim:
1. Amino-oxazole derivatives of the formula:

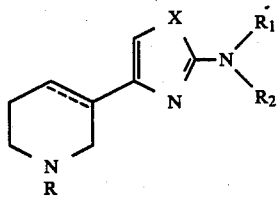

wherein:
R represents hydrogen;
X represents oxygen;
R₁ and R₂ represent hydrogen or alkyl (1–4 C), and the dotted line represents an optional extra bond, as well as pharmaceutically acceptable acid addition salts thereof.

2. Compounds according to claim 1, in which the dotted line is an extra bond, and pharmaceutically acceptable salts thereof.

3. Compounds according to claim 1, in which R₁ and R₂ represent both hydrogen and pharmaceutically acceptable salts thereof.

4. Pharmaceutical composition comprising an effective amount of the compound of claim 1 to provide dopamineagonist activity when administered to a patient, together with one or more pharmaceutically acceptable carriers or diluents.

* * * * *